United States Patent [19]

Lange et al.

[11] Patent Number: 4,874,554
[45] Date of Patent: Oct. 17, 1989

[54] QUATERNARY AMMONIUM COMPOUNDS

[75] Inventors: Fritz Lange, Essen; Peter Busch, Erkrath; Klaus Thiele, Langenfeld, all of Fed. Rep. of Germany

[73] Assignee: Henkel Kommanditgesellschaft auf Aktien, Duesseldorf, Fed. Rep. of Germany

[21] Appl. No.: 72,379

[22] Filed: Jul. 10, 1987

[30] Foreign Application Priority Data

Jul. 10, 1986 [DE] Fed. Rep. of Germany ....... 3623215

[51] Int. Cl.$^4$ ........................................... C07C 107/08
[52] U.S. Cl. .................................. 260/404; 560/250; 560/252; 560/253
[58] Field of Search ................ 260/404; 560/252, 253, 560/250

[56] References Cited

U.S. PATENT DOCUMENTS 2,653,156  9/1953  Deutsch et al. ................. 560/253 X
4,638,089  1/1987  Hisamoto et al. .............. 560/253 X

FOREIGN PATENT DOCUMENTS 0102140  3/1984  European Pat. Off. .
3504242  8/1986  Fed. Rep. of Germany .
1087413  10/1967  United Kingdom .

OTHER PUBLICATIONS

Garson, L. R., J. Med. Chem., 12, 538-40 (1969).

Primary Examiner—Paul J. Killos
Attorney, Agent, or Firm—Wayne C. Jaeschke; Henry E. Millson, Jr.; Norvell E. Wisdom, Jr.

[57] ABSTRACT

Quaternary ammonium compounds corresponding to the formula

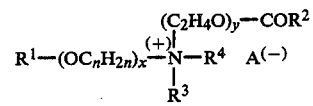

are produced by esterification of ether amines corresponding to the formula

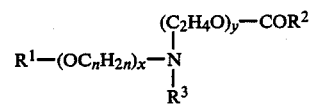

with a fatty acid of the formula $R^2$—COOH and quaternization of the product obtained with an alkyl halide or a dialkyl sulfate. They are suitable for use as conditioning and revitalizing agents in hair-cosmetic preparations.

5 Claims, No Drawings

QUATERNARY AMMONIUM COMPOUNDS

BACKGROUND OF THE INVENTION

1. Field of the Invention

This invention relates to new quaternary ammonium compounds as well as to their use as hair-conditioning and combability-improving additives in hair-cosmetic preparations.

2. Statement of Related Art

Cationic surfactants of the quaternary ammonium compound type are used in hair cosmetics as revitalizing and conditioning agents for improving the combability, body and feel of the hair and for reducing its static charge. The products are normally used in hair aftertreatment preparations (conditioners) which, after washing of the hair, are intended to restore favorable hair-cosmetic properties. However, such compounds are not suitable as conditioner additives in shampoos themselves, because most of the known quaternary ammonium compounds are incompatible with the high-foam anionic surfactants normally used in shampoos. When present in the concentrations required for an adequate conditioning effect, they form substantially water-insoluble and cosmetically ineffectual deposits. Quaternary ammonium compounds which are more compatible with anionic surfactants generally have an inadequate conditioning effect.

Although water-soluble cationic polymers are generally compatible with anionic surfactants, they are attended by other disadvantages, such as accumulation on the hair after repeated treatment resulting in dullness, and inadequate antistatic effects on dry hair.

DESCRIPTION OF THE INVENTION

Other than in the operating examples, or where otherwise indicated, all numbers expressing quantities of ingredients or reaction conditions used herein are to be understood as modified in all instances by the term "about".

The present invention provides novel quaternary ammonium compounds, which have strong revitalizing and conditioning properties on human hair and which may even be incorporated in shampoos based on high-foam anionic surfactants in conditioner effective concentrations, without negative effects.

The new quaternary ammonium compounds have the following formula

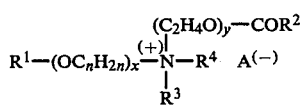

wherein $R^1$ is a $C_{8-22}$ alkyl, $R^2$ is a $C_{7-21}$ alkyl, $R^3$ is a $C_{1-4}$ alkyl, $-(C_2H_4O)_z-H$, or $-(C_2H_4O)_z-COR^2$, $R^4$ is a $C_{1-4}$ alkyl or benzyl, n is 2 or 3, x is 0 or a number from 1 to 10, y and z are numbers from 1 to 10 and A is chloride, bromide, or an anion of the formula $R^5O-SO_3(-)$ where $R^5$ is a $C_{1-4}$ alkyl.

The quaternary ammonium compounds are produced from ether amines corresponding to the formula

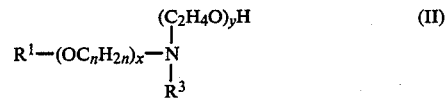

wherein $R^3$ is $C_{1-4}$ alkyl or $-(C_2H_4O)_z-H$, and $R^1$, n, x, y and z are as defined for formula I. The preparation is by esterification with a fatty acid of the formula $R^2-$COOH, where $R^2$ is as defined for formula I, under known reaction conditions. The quaternization of the product obtained is with an alkyl halide or a dialkyl sulfate of the formula $R^4A$ where $R^4$ and A are as defined for formula I.

Ether amines corresponding to formula II are known from the literature, for example from published British patent application No. 1,087,413 and from published European patent application No. 102,140. In the process described therein, the ether amines in question are prepared from primary and secondary amines by alkylation at the nitrogen atom, with alkyl polyglycol ether sulfates. Another process, which is the subject of German patent application No. 35 04 242, which was published 14 Aug. 1986, subsequent to the original German patent application for the present invention, starts out from tertiary alkanolamines and leads to ether amines corresponding to formula II by alkylation at the hydroxyl group, with alkyl sulfates or alkyl polyglycol ether sulfates.

Compounds corresponding to formula II, in which y (and/or z) has values of greater than 1 may be obtained by reaction of ether amines corresponding to formula II, in which y (and/or z) is 1, with $(y-1)+(z-1)$ mols ethylene oxide by the relevant known process. The hydrophilicity of the quaternary ammonium compounds according to the invention may be adjusted within wide limits in this manner.

The esterification of the ether amines corresponding to formula II with fatty acid is carried out by generally known esterification processes, for example in the presence of typical basic esterification catalysts, preferably tin powder or tin oxide. Suitable fatty acids are any of the fatty acids occurring in natural fats, such as n-octanoic acid (caprylic acid), n-decanoic acid (capric acid), n-dodecanoic acid (lauric acid), n-tetradecanoic acid (myristic acid), n-hexadecanoic acid (palmitic acid), n-octadecanoic acid (stearic acid), oleic acid, linoleic acid, arachic acid, erucic acid or behenic acid. Synthetic and optionally branched $C_{8-22}$ fatty acids and mixtures of individual representatives of the fatty acids mentioned are also suitable. The esterification is generally carried out with equimolar quantities of the fatty acid, based on the free hydroxyl groups. Where $R^3$ is $-(C_2H_4O)_z-H$, from 1 to 2 mols fatty acid may be used for the esterification.

The quaternization is also carried out by known methods. Suitable quaternizing agents are alkyl chlorides, alkyl bromides, $C_{1-4}$ dialkyl sulfates, benzyl chloride or benzyl bromide.

The quaternary ammonium compounds according to the invention have surface-active properties and, like all quaternary ammonium compounds, are substantive, i.e. they become attached to fiber surfaces where they show antistatic and revitalizing properties. In addition, they may be clearly solubilized in aqueous surfactant solutions. Most surprisingly, the quaternary ammonium compounds according to the invention may even be solubilized in aqueous solutions of anionic surfactants to form clear or only faintly opal solutions without any substantially insoluble electroneutral salts being formed. This property makes any quaternary ammonium according to the invention, or a combination of one or more thereof, particularly suitable for use as a conditioning and revitalizing agent in hair-cosmetic preparations.

In the context of the invention, hair-cosmetic preparations are understood to be any aqueous or aqueous alcoholic preparations which are suitable for the caring and decorative treatment of human hair, such as hair washes, hair lotions, hair cures, hair lacquers, hair dyes, permanent waving lotions, hair aftertreatment preparations (conditioners), hair rinses and shampoos or their mixtures. The compounds of this invention are included within the foregoing preparations in respectively conditioner effective amounts, i.e. hair wash conditioner-effective, hair lotion conditioner-effective, etc.

Particularly preferred embodiments of the invention are aqueous shampoos containing from 5 to 25% by weight anionic sulfate and/or sulfonate surfactants and a conditioner/antistatic effective amount, preferably from 0.1 to 5% by weight of at least one quaternary ammonium compound corresponding to formula I. By anionic sulfate or sulfonate surfactants are meant alkali and/or mono-, di- or tri-$C_{2-3}$ alkanolamine salts, of surface-active compounds which contain a completely or predominantly linear $C_{10-16}$ alkyl and an anionic —$SO_3(-)$ or —$OSO_3(-)$ moiety in the molecule. Preferred examples of sulfate or sulfonate surfactants such as these are at least one of fatty alcohol sulfates, fatty alcohol polyglycol ether sulfates (containing from 1 to 12 glycol ether groups), secondary alkane sulfonates and alpha-olefin sulfonates.

According to the invention, quaternary ammonium compounds corresponding to formula I, in which y and z=1, $R^4$ is a methyl group and A is chloride anion, are particularly suitable.

The following Examples illustrate the invention without limiting it in any way.

EXAMPLES

1. Cocos-($C_{12-18}$)-alkyl poly(6)oxyethyl di-(2-lauroyl-oxyethyl)-methyl ammonium chloride 1.1 Esterification 800 g (1.183 mols) cocos-($C_{12-18}$)-alkyl poly(6)-oxyethyl dihydroxyethyl amine (amine number 83, prepared from cocos-($C_{12-18}$)-alkyl+6 EO sulfate, sodium salt, and diethanolamine) and 472.2 g (2.366 mols) lauric acid were heated to 220° C. on a water separator in the presence of 20 g tin powder and stirred for 2 hours at that temperature until the elimination of water was over. The reaction mixture was then filtered off from the tin powder. A clear, viscous brown-yellow oil having a residual acid number of 1.38 was obtained.

1.2 Quaternization 600 g of the reaction product from 1.1 were reacted with methyl chloride in a pressure autoclave at 90° C./10 bar. After about 5 hours, no more methyl chloride was being taken up and the amine number of the reaction mixture had fallen to 2.2. A brown wax-like product was obtained.

2. Cocos-($C_{12-18}$)-alkyl poly(6)oxyethyl-2-lauroyloxyethyl-2-hydroxyethyl methyl ammonium chloride 2.1 Esterification 1000 g (1.48 mols) cocos-($C_{12-18}$)-alkyl poly(6)oxyethyl dihydroxyethylamine (amine number 83, prepared from cocos-($C_{12-18}$)-alkyl+6 EO sulfate, sodium salt, and diethanolamine) and 295 g (1.48 mols) lauric acid were heated to 200° C. on a water separator in the presence of 20 g tin powder and stirred for 2 hours at that temperature until the elimination of water was over. The reaction mixture was then filtered off from the tin powder through diatomaceous earth. A clear, yellow-brown viscous oil having a residual acid number of 1.0 was obtained.

2.2 Quaternization 900 g of the reaction product from 2.1 were reacted with methyl chloride in a pressure autoclave at 80° C./5 bar until methyl chloride was no longer taken up and the amine number had fallen to 2.4 (after about 8 hours). A brown wax-like product was obtained.

3. Lauryl myristyl poly(3)oxyethyl di-(2-lauroyloxyethyl)-methyl ammonium chloride 3.1 Alkylation 968 g (1.67 mols) $C_{12-14}$ fatty alcohol (7:3) 2 EO sulfate, Na salt (65.8% aqueous solution) were combined with 300.7 g (2.018 mols) triethanolamine and substantially dehydrated in a water jet vacuum at 100° C. in a rotary evaporateor. After the reaction vessel had been purged with nitrogen, 80.7 g (2.018 mols) sodium hydroxide were added and, after purging with more nitrogen, the reaction mixture was heated for 3 hours to 200° C. After cooling to 20° C., the mixture was repeatedly washed with saturated sodium chloride solution and dried in vacuo with heating to 100° C. in a rotary evaporator. A yellow-brown oil having an amine number of 111.4 (lauryl myristyl poly(3)oxyethyl dihydroxyethylamine) was obtained in a quantity of 565 g.

3.2 Esterification 240 g of this product (0.483 mol) and 193.3 g lauric acid (0.966 mol) were heated to 170° C. on a water separator in the presence of 4.5 g tin powder and stirred for 3 hours at that temperature until the elimination of water was over. The reaction mixture was then filtered off from the tin powder. A clear, viscous brown-yellow oil was obtained in a quantity of 404 g (acid number=0).

3.3 Quaternization 300 g of the reaction product from 3.2 were reacted with methyl chloride in a pressure autoclave at 90° C./10 bar. After 3 hours, the temperature was increased to 110° C.; after another 3 hours, no more methylene chloride was being taken up. The amine number of the reaction mixture was 10. A brown-wax like product was obtained.

4. Octyl-2-lauroyloxyethyl-2-hydroxyethyl methyl ammonium chloride 4.1 Esterification 250 g (1.142 mols) octyl diethanolamine (amine number 249.6, prepared from n-octanol-1 and diethanolamine) and 228.7 g (1.142 mol) lauric acid were heated to 160° C. on a water separator in the presence of 5.0 g tin powder. After 2 hours, the elimination of water was over. After cooling to room temperature, the reaction product was filtered off from the tin powder. A clear, viscous oil having a residual number of 2.7 was obtained in a quantity of 380 g.

4.2 Quaternization 300 g of the esterification product from 4.1 were reacted with methyl chloride in a pressure autoclave at 90° C./5 bar. After about 10 hours, no more methyl chloride was being taken up and the amine number of the reaction mixture had fallen to 5. A brownish, wax-like product was obtained.

5. Hair-cosmetic testing

The quaternary ammonium compounds according to the invention prepared in Examples 1 and 2 were incorporated in formulations 5.2 and 5.3 of the Table and performance-tested for their effectiveness in improving wet combability against (a) a standard shampoo (formulation 5.1) without ay quaternary ammonium compounds and (b) a comparison shampoo containing cetyl trimethyl ammonium chloride (formulation 5.4).

6. Measurement of wet combability (laboratory test)

Standardized strands of hair predamaged under defined conditions by bleaching and cold waving were used. The strands were shampooed in lukewarm water with the shampoos indicated in the Table in a quantity of 1 g per g hair and rinsed with clear water. Wet combability was determined by measurement of the combing resistance i.e. the force required to draw a comb through a tuft of hair, using a modified draw testing machine of the 1402 type manufactured by the Zwick company (Einsingen in Ulm/Donau, Germany). The test arrangement is described in "Riechstoffe, Aromen, Kosmetika" no. 12, (1977), page 325, columns 2 and 3, a lower value (% combing resistance) being preferred.

To minimize errors, the combing resistance was determined 15 times with each of the shampoos to be tested and the average values formed. The measured average combing resistance values were expressed in percent of the standard. The standard was determined after shampooing with shampoo 5.1 (free from quaternary ammonium compounds) and rinsing with clear water.

The results of the test are shown in the following Table:

TABLE

| | EXAMPLE | | | |
|---|---|---|---|---|
| Test shampoos | 5.1 | 5.2 (invention) | 5.3 (invention) | 5.4 |
| Fatty alcohol (C$_{12-14}$) + 2 EO sulfate, Na salt (28%) | 50 | 50 | 50 | 50 |
| QUAT Example 1 | — | 2 | — | — |
| QUAT Example 2 | — | — | 2 | — |
| Cetyl trimethyl ammonium chloride | — | — | — | 2 |
| Water (fully deionized) | 50 | 48 | 48 | 48 |
| Appearance at 20° C. | clear | clear | clear | cloudy (sediment) |
| Wet combability (% combing resistance) | 100 | 70 | 93 | 88 |

As can be seen from the above, the product of comparative example 5.4 had a cloudy appearance and a sediment, resulting in a totally unacceptable product. Moreover, its combing resistance was relatively high, although acceptable. Comparative example 5.1, although clear, had an unacceptably high combing resistance, indicating no hair treating qualities as desired in this invention. Examples 5.2 and 5.3, according to the invention and representative of its novel compounds, were not only clear, but also had desireably reduced combing resistance.

We claim:

1. A quaternary ammonium compound of the formula:

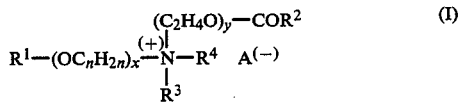

wherein:
$R^1$ is a $C_{8-22}$ alkyl;
$R^2$ is a $C_{7-21}$ alkyl;
$R^3$ is a $-(C_2H_4O)_z-H$, or $-(C_2H_4O)_z-COR^2$;
$R^4$ is a $C_{1-4}$ alkyl or benzyl;
n is 2 or 3;
x is a number from 1 to 10;
y and z are each a number from 1 to 10; and
A is chloride, bromide, or $R^5OSO_3(-)$ where $R^5$ is a $C_{1-4}$ alkyl.

2. The compound of claim 1 wherein y and z are each, 1, $R^4$ is methyl, and A is chloride.

3. The compound of claim 1 having the formula: cocos-(C$_{12-18}$)-alkyl poly(6)oxyethyl di-(2-lauroyloxyethyl)-methyl ammonium chloride.

4. The compound of claim 1 having the formula: cocos-(C$_{12-18}$)-alkyl poly(6)oxyethyl-2-lauroyloxyethyl-2-hydroxyethyl-methyl ammonium chloride.

5. The compound of claim 1 having the formula: lauryl myristyl poly(3)oxyethyl di-(2-lauroyloxyethyl)-methyl ammonium chloride.

* * * * *